United States Patent [19]

Lindow

[11] 4,432,160
[45] Feb. 21, 1984

[54] MICRORGANISM INHIBITION OF FROST DAMAGE TO PLANTS

[75] Inventor: Steven E. Lindow, Berkeley, Calif.

[73] Assignee: The Regents of the University of California, Berkeley, Calif.

[21] Appl. No.: 294,604

[22] Filed: Aug. 20, 1981

[51] Int. Cl.$^3$ .............................................. A01G 1/00
[52] U.S. Cl. ........................................................ 47/2
[58] Field of Search .............................................. 47/2

[56] References Cited

U.S. PATENT DOCUMENTS 4,161,084  7/1979  Arny et al. ................................ 47/2

OTHER PUBLICATIONS

Arny et al., "Frost sensitivity of *Zea mays* increased by application of *Pseudomonas syringae*", *Nature* (1976) 262:282–284.
Lindow et al., "Distribution of epiphytic ice nucleation-active strains of *Pseudomonas Syringae*", *PAPSD* 4, 1977:107.
Lindow et al., "Bacterial ice nuclei as incitants of warm temperature frost damage", *PAPSD* 3, 1976:224.
Lindow, S. E., "Frost damage to potato reduced by bacteria antagonistic to ice nucleation-active bacteria", 71st mtg of the Amer. Phytopathological Soc. 69 (9) 1979, p. 1036.
Lindow et al., "Antagonistic bacteria reduce bacterially incited frost damage to corn (*Zea mays* L.)", Control of frost damage to corn in the field by a bacterium antagonistic to ice nucleation-active bacteria, *PAPSD* 4, (1977):169.
Lindow et al., "Increased frost sensitivity of maize in the presence of *Pseudomonas syringae*", *PAPSD* 2, (1975):57.
Lindow et al., "Distribution of ice nucleation-active bacteria on plants in nature", *Applied and Environmental Microbiology* (1978) 36:831–838.
Lindow et al., "Erwina herbicola: A bacterial ice nucleus active in increasing frost injury to corn", *Phytopathology* (1978) 68:523–527.
Hirano et al., "Ice nucleation activity of fluorescent plant pathogenic pseudomonads", Proc. 4th Int. Conf. Plant. Path. Bact., (1978) pp. 717–724.
Lindow et al., "The role of bacterial ice nuclei in frost injury to sensitive plants", *Plant Cold Hardiness and Freezing Stress*, (1978) pp. 249–263.
Lindow et al., "Leaf surface bacterial ice nuclei as incitants of frost damage to corn and other plants", *PLPHA* 59 (6 Suppl) (1977):4.

*Primary Examiner*—Robert E. Bagwill
*Attorney, Agent, or Firm*—Bertram I. Rowland

[57] ABSTRACT

Plant host acceptable microorganisms, which are ice nucleation deficient and use at least one nutrient from the plant also used by ice nucleating native microorganisms, are applied to a plant part at an early stage in the growth cycle. The multiplication of the native ice nucleating microorganisms is inhibited, so that under normal frost conditions encountered in the field, frost damage is substantially diminished. The non-nucleating microorganisms may be obtained by special selection procedures, selecting from naturally occurring microorganisms or mutagenized microorganisms, where additionally the organisms may be transformed to provide for other desirable properties.

The following organisms have been deposited at the A.T.C.C. on Aug. 13, 1981; A5-01, A5-05-1, A5-06, A5-10-1, A5-26, and A4-2B-10.

17 Claims, No Drawings

MICRORGANISM INHIBITION OF FROST DAMAGE TO PLANTS

BACKGROUND OF THE INVENTION

1. Field of the Invention

Frost sensitive agricultural plants are damaged when ice formation occurs within their tissues. Ice formation within the tissues causes a mechanical disruption of the cells giving rise to the symptoms known as frost injury. Most frost sensitive agricultural plants have no mechanism to tolerate the formation of ice within their tissues; whenever ice formation occurs within these tissues, frost injury results. Thus, these plant species have no mechanism for frost tolerance. However, it has been shown that the water within the plant tissues of these species has the innate ability to supercool, that is, to remain in a liquid state at temperatures below 0° C. Certain species of bacteria have the property of ice nucleation so that their presence on the surface of the plants limits the ability of the water to supercool. *Pseudomonas syringae, Erwinia herbicola* or certain strains of *Pseudomonas fluorescens,* catalyze ice formation limiting supercooling to less than 1° C.

It would therefore be desirable to develop economic and efficient means for preventing the ice nucleation caused by these microorganisms without harming the plant host and maintaining the protection during the period when the plant is subject to frost injury.

2. Description of the Prior Art

A paper was presented by Lindow, S. E., entitled, "Frost Damage To Pear Reduced by Antagonistic Bacteria, Bactericides and Ice Nucleation Inhibitors", Am. Phytopah Soc. Annual Meeting, Aug. 23-28, 1980. U.S. Pat. Nos. 4,045,910 and 4,161,084 describe the use of ice nucleating deficient microorganisms to inhibit frost injury.

SUMMARY OF THE INVENTION

Method, compositions and microorganisms are provided for inhibiting ice nucleation. Nucleation deficient microorganisms capable of growing on a host plant are selected which compete with nucleation capable microorganisms, particularly for at least one essential limited nutrient supplied by the host plant. The nucleation deficient microorganisms are applied to the plant at an early stage in the growth cycle, so as to become established and inhibit the presence and establishment of nucleation capable microorganisms. The organisms may be selected from natural sources or from mutagenized sources and may be further modified by transformation to impart specific desirable properties. Benefits other than inhibition of frost injury have been observed.

DESCRIPTION OF THE SPECIFIC EMBODIMENTS

Frost injury of host plants is inhibited by providing for the establishment of nucleation deficient microorganisms capable of growing on the host and antagonistic to the nucleation capable microorganisms native to the host. The nucleation deficient microorganisms are selected from native or mutagenized microorganisms by a method which establishes their antagonistic capability to the nucleation capable microorganisms. The desirable properties of the nucleation deficient organisms may be further enhanced by transformation to introduce specific genetic capabilities. The nucleation deficient microorganisms are applied to the host plant at an early stage in the growth cycle and prior to or during the period when frost damage may be encountered.

The nucleation deficient microorganisms may be obtained from endogenous microorganisms of the plant or mutagenized organisms or any other source and selected by a test procedure which discriminates between ice nucleation-capable and ice nucleation-deficient bacterial species. The mutagenesis may be by any convenient method, including chemical, such as with ethyl methanesulfonate or nitrosoguanidine, or by irradiation with ultra-violet or x-ray radiation. For the natural microorganisms, the predominant microflora on healthy leaves of frost sensitive agricultural plants are isolated.

The microorganisms or bacteria may be any microorganisms which populate plants and which increase in population during plant growth. In view of the wide variety of species and strains which may be employed as antagonists, no single species can be indicated as the sole species to be used as antagonists. Of particular interest are strains of Pseudomonas, Erwinia, Corynebacterium, Xanthomonas and Bacillus.

The procedure for selection initially spots the microorganisms onto the surface of a defined medium encompassing the relative proportion of limited nutrients normally found on host leaf surfaces. By limited is intended that the amount available limits the overall cell population on the surface. The medium normally includes a mixture of sugars and amino acids, particularly the dicarboxylic amino acids and their monoamides, which appear to be utilized by the microflora on the host and in limited availability to the microflora. Normally, also included will be one or more uronic acids and inorganic salts. These are incorporated into an appropriate gel e.g. agar. Of the active ingredients, the sugars will be present in the range of about 80–95 weight percent, while the total amino acids and the total inorganic salts will each be present in the range of about 2–10 weight percent. The total amount of nutrients will generally be about 0.01 to 2, usually about 0.1 to 1 weight percent of the gel medium.

The medium employed supports a limited growth of most randomly selected leaf surface bacteria. Bacteria which grow on this nutrient medium deplete the medium of selected nutrients in a zone around their area of growth. The randomly spotted antagonistic microorganisms which deplete nutrients which are critical for the survival and growth of ice nucleating bacteria can be selected by growing the bacteria on the gel nutrient medium surface to establish colonies and deplete the nutrient source.

The surface supporting the colonies are then oversprayed with a suspension of ice nucleating cells, such as *P. syringae* or *E. herbicola.* The ice nucleating bacteria atomized over the surface of the plates will grow in the areas in between the spotted areas containing antagonistic bacteria. An antagonistic baterium is adapted for utilizing nutrients required for growth and limiting for growth of ice nucleating bacteria. The antagonistic bacteria are indicated by a clear zone resulting from no growth from the applied ice nucleating bacteria surrounding the patch area on the surface of the nutrient surface spotted with the antagonistic bacteria.

Antagonistic bacteria giving a positive reaction in the above test are verified as not producing antibiotic substances which would also inhibit the growth of ice nucleating bacteria in such a radial diffusion test. This is done by spotting selected antagonist bacteria, both on the limited medium as described above and on a nutrient rich medium such as King's Medium B. The procedure is performed as described above and the presence or absence of growth in the medium immediately surrounding the spotted colony is scored. Antagonistic bacteria which inhibit growth on the limited medium, but not on King's B medium indicate isolates which utilize critical nutrients limiting the growth of the ice nucleating bacteria.

The antagonist would then be further selected and screened in a greenhouse and laboratory procedure. The plant host at an early stage of growth would be sprayed with a suspension of the selected antagonist and growth permitted for a limited period of time. Inoculated plants and plants which were not inoculated, but used as controls, would then be inoculated with ice nucleating bacteria capable of growing on the host. After incubation in a moist chamber for a relatively short time, the plants would be allowed to dry and placed in a controlled environmental chamber at approximately $-5°$ C. After about a 1 hr. exposure at $-5°$ C., all plants would be incubated at growth conditions e.g. $20°$ C., for 1 day, at which time the leaves which had symptoms of frost injury, dark water-soaked and flaccid leaves, would be rated. Significant reduction in the presence of water-soaked leaves would be indicative of effective antagonistic bacteria.

Where the cells are derived from mutagenesis of ice nucleation capable strains, a different procedure may be employed for screening ice nucleation deficient cells. The mutagenized cell mixture is plated onto an appropriate nutrient medium gel surface and after a limited growth period, they are replicated onto the surface of paraffin coated aluminum foil which is then maintained at an ice forming temperature, e.g. $-5°$ or $-9°$ C. Colonies retaining the wild type ice nucleation activity immediately freeze and may be distinguished from mutants which lack the ice nucleation activity. These mutants remain liquid when small droplets of water are atomized over the surface of these sheets. These mutants may then be further tested as described above to insure their absence of ice nucleation capability, while retaining their host range and capability of successful competition with the wild type strain.

The ice nucleation deficient microorganisms may be modified in accordance with conventional techniques to introduce novel genetic capabilities. These techniques, for the most part, involve transformation, transduction and conjugation. Various genetic capabilities which can provide advantages for the antagonist microorganism include imparting antibiotic resistance, bacteriocin production, host range, growth characteristics, e.g. colicin nitrogen fixation, or the like. By providing for a marker which allows for selection of transformants or conjugants, the desired organisms may then be selected. Markers include antibiotic resistance, colicin resistance, heavy metal resistance, providing prototrophy to auxotrophs, or the like.

The subject bacteria may be employed with a wide variety of crop plants, particularly vegetables, fruits, grains and nut trees. Included among the plant hosts are citrus, such as lemons, oranges, e.g. navel oranges, grapefruit, and the like; pears, almonds, tomatoes, potatoes, grains, legumes, e.g. soybean, and the like.

Depending upon the nature of the plant, the part of the plant to which the antagonistic microorganism is applied, as well as other factors, a variety of methods and compositions may be employed for application of the organism to the plant. In addition, it may be desirable to use mixtures of organisms, 2 or more, rather than a single organism.

The number of cells per unit formulation will depend on whether the formulation is a dry or wet formulation. For wet formulation, e.g. foliar sprays, suspensions, aerosols, mist, etc., the number of cells per ml will generally be from about $10^5$ to $10^{10}$ cells per ml. Generally, it is desired to have about $10^4$ to $10^{10}$ cells/g fr. wt. of leaves during application. For dry formulations, the number of cells will generally range from about $10^4$ to $10^9$ cells/g of formulated product. The cells in the formulation should provide a sufficient number of cells to allow the cells to become established on the host plant in competition with microorganisms present in the native environment taking into consideration the mortality rate, higher with spray formulations, which are encountered with the means of administration. The number of cells should be sufficient to colonize within about one week or less for sprays.

In aqueous formulations various additives may be included in minor amounts such as surfactants, e.g. nonionic, dyes, nutrients, buffers, penetrating agents for introducing the cells into the leaf, biological or chemical pesticides e.g. herbicides, insecticides, etc. In dry formulations various additives include inert powders, bacterial stabilizing agents, salts, anticaking agents, nutrients, buffers, film forming materials, biological or chemical pesticides e.g. herbicides, insecticides, etc. The various additives will range in concentration from about $1\times10^{-4}$ to 1 weight percent.

Other additives may also be included for specific situations, one of which will be discussed hereafter.

One technique is to apply the antagonistic bacteria to the seed (seen inoculant) or seed piece of a plant. The bacteria may be formulated as a dry powder formulation in accordance with conventional techniques. Of particular interest is a powder formulation containing the cells which is derived from combining about one part by volume of a cell containing gum suspension, with 4 volumes of an inert powdered carrier e.g. talc. The gum suspension is prepared by combining about 1 vol. of a dense suspension of cells (about $10^9$–$10^{11}$ cells/ml) with about 10 vols. of a dilute magnesium salt solution, which mixture is then combined with 10 vols of a thick aqueous suspension of a natural gum. The gum will be about 90-99% by weight of the mixture and employed initially as a 10-30 weight percent suspension. The mixture is allowed to dry and ground to a fine powdered consistency. The seeds or seed pieces in a slightly moistened state are contacted with the powder. Upon planting, it is found that the bacteria colonize the emerging stem and leaves as they emerge from the soil.

The powder formulation may also be applied as a dust application. Conveniently, the bacteria are applied to the foliage at a rate of from about $10^7$ to $10^8$ bacteria per gram fr. wt. of leaves being inoculated. The use of the dust powder inoculation is particularly applicable during hot weather, on bright sunny days, when applied prior to mid to late afternoon and at low relative humidities.

Another popular way for establishing the antagonistic bacteria is by foliar spray. The antagonistic bacteria need only be employed as an aqueous suspension, in substantial absence of other additives, e.g. nutrients and surfactants. The application rate will generally be approximately $10^6$ to $10^8$ cell/ml of vegetative cells in an aqueous suspension to provide about $10^4$ to $10^8$ cells/g. fr. wt. of leaves.

Where the antagonistic microorganisms are biocidally resistant, either as the wild strain or due to transformation, a biocide may be included in a formulation, particularly where the application is at a time in the growth stage where ice nucleation capable bacteria may have become established. By utilizing the biocide, the established ice nucleation bacteria may be killed, providing a niche for the ice nucleating deficient bacteria which may then become established and inhibit the reestablishment of the ice nucleating bacteria. Illustration of biocides are antibiotics, toxins and the like. Particular antibiotics include streptomycin, oxytetracycline, tetracycline, kanamycin and the like. The amount of antibiotic will vary widely depending on the antibiotic, but will generally be in amounts of from about 50 to 100 ppm of formulation.

In order to demonstrate the subject invention, the following examples were carried out. The following examples are offered by way of illustration and not by way of limitation.

EXPERIMENTAL

Predominant microflora on healthy leaves of selected frost sensitive agricultural plants were employed for the isolation of ice nucleating deficient bacteria. The following medium was employed to provide quantities of carbohydrate nitrogen sources that are normally leached from the surfaces of the plants. The following quantities of materials were present per liter of medium or for more stressing conditions, the medium may be diluted up to 10-fold.

TABLE 1

| | g | | mg |
|---|---|---|---|
| Sugars | | Amino Acids | |
| Sucrose | 3 | Aspargine | 30 |
| Fructose | 1 | Glutamine | 50 |
| Glucose | 1 | Glutamic acid | 50 |
| | | Aspartic acid | 110 |
| Uronic Acid | | Inorganic Salts | |
| Galacturonic acid | 0.1 | Dibasic potassium phosphate | 100 |
| Agar | 15 | Magnesium sulfate | 50 |

Plates of the above medium are started and colonies allowed to grow for two days at 24° C. The plate is then oversprayed with a suspension of approximately $10^8$ cells/ml of either *P. syringae* or *E. herbicola.* A positive indication for antagonistic bacteria is indicated by a clear zone resulting from no growth of the applied ice nucleating bacteria surrounding the patched area on the surface of the agar plate spotted with the antagonistic bacteria.

To insure that the desired result would not be excretion of antibiotic by the antagonistic bacteria, the following experiment was carried out.

The selected antagonist was spotted on the above indicated medium and the nutrient rich medium King's Medium B and the procedure repeated with both plates with scoring for the absence or presence of growth in the area immediately surrounding the spotted colony. Antagonist which inhibited growth on the limited medium, but not on the nutrient rich medium, indicated isolates which utilized critical nutrients limiting growth of the ice nucleating bacteria. These isolates were further screened in a greenhouse and laboratory procedure.

One hundred three-leaf stage corn seedlings were sprayed with the suspension of approximately $10^8$ cells/ml of the selected antagonist and placed in a moist chamber in a greenhouse at approximately 24° C. for 2 days. These plants and controls, plants that did not receive a pretreatment with antagonistic bacteria, were then inoculated by spraying approximately $10^5$ cells/ml of *P. syringae* on the leaf surfaces. After incubating the plants in the moist chamber for 2 days, the plants were then allowed to dry and placed in a controlled environmental chamber at approximately −5° C. After a 1 hour exposure to −5° C., all plants were allowed to incubate at 20° C. for 1 day. The dark water-soaked and flaccid leaves which resulted and were indicative of frost injury were then rated. Reduction in the presence of water-soaked leaves on plants pretreated with antagonistic bacteria as compared to plants which were not pretreated with the antagonistic bacteria indicated effective antagonistic bacteria resulting in reduced frost injury.

In the following experiment mutagens were selected. Two strains of *P syringae* which were capable of ice nucleation, labeled strains 31 rif 1 and 422 B, isolated from corn and almond respectively, were mutated in accordance with conventional techniques employing ethyl methanesulfonate as the mutagen. The resulting mutagenized culture was plated onto a rich nutrient agar medium, such as Kings Medium B, with approximately 50 cells per plate. The colonies were allowed to grow for approximately 24 hours or until their colony diameter was about 1 millimeter, at which time they were replicated using a piece of sterile velvet onto the surface of a paraffin coated aluminum foil. The foil was then placed on the surface of a refrigerated constant temperature bath at −5° or −9° C. Colonies which retained the wild type ice nucleation activity immediately froze and were distinguishable from mutants which lacked ice nucleation activity at either −5° or at −9° C. The latter remained liquid when small droplets of water were atomized over the surface of these sheets. The ice nucleation deficient cells were selected, recultured, purified and independently verified to completely lack ice nucleation activity at temperatures above 5°. They were further tested for antagonism in vivo by the above described procedure.

Ice nucleation deficient mutants of *P syringae* and *E. herbicola* were detected and isolated by a replica freezing technique at a frequency of about $4\times10^{-3}$ from ethyl methanesulfonate mutagenized cells. The nucleation characteristics of 53 *P. syringae* and 27 *E. herbicola* mutants, measured as the fraction of cells active in the ice nucleation as a function of temperature (nucleation frequency) was determined. Mutants exhibited reduced threshhold temperatures of nucleation (−3° C. to 8.4° C.) compared with parental type strains (−1.2° C.) and a reduction of nucleation frequency by a factor of $10^3$ to $10^8$ at temperatures above −5° C. or at −9° C. compared with parental strains or a combination of both of these characteristics. *P. syringae* and *E. herbicola* were respectively transformed by the plasmids RSF1010 ($10^2$ to $10^3$ transformants/mg DNA) and pBR322 to provide streptomycin and oxytetracycline resistance respectively.

In order to establish the utility of the isolated strains, the strains were tested under field conditions. A single application of the strains, singly or in combination, as early as possible in the life stage of the plant, in most cases was found sufficient to achieve frost control throughout the period of maximum frost hazard to these plants. In most cases it was found sufficient to apply the bacteria as a foliar spray to the foliage of newly emerging seedlings or flowers of deciduous trees. Bacteria were applied at the rate of approximately $10^6$ to $10^8$ cells/ml of vegetative cells in an aqueous suspension. In some instances, antibiotics such as streptomycin or oxytetracycline were included in the aqueous suspension, where the ice nucleation deficient strains were antibiotic resistant. The presence of these antibiotics aided in antagonist establishment in the plants.

Instead of foliar sprays, a dried powdered formulation was employed with the seed and seed pieces. The formulation was prepared as follows. Vegetative cells of the antagonistic bacteria were made into a dense suspension, greater than $10^{12}$ cells/ml, mixed with 10 vols of 0.1 M magnesium sulfate and the mixture incorporated into 10 vols of a 20% aqueous suspension of xanthan gum. After thorough mixing of the gum with the bacterial cell suspension, talc was incorporated in four parts per part of gum (v/v). After allowing the mixture to dry at 10° C. for 10 days, it was then ground to the consistency of a fine powder.

Potato seed pieces (slightly moistened) were then rolled in the presence of this dried powdered formulation and then planted. The bacteria were found to colonize the emerging stem and leaves as they emerged from the soil and reduction in frost injury was observed. In addition it was found that the bacteria also colonized the roots and enhanced the growth and formation of stolons and young daugther tubers on these plants. The evidence also indicated that some modest degree of growth response occurred.

Where the antagonistic bacteria were applied at 10% bloom to fruit crops, such as pear and almond, it was observed that there was a reduction in disease symptoms, such as fireblight resulting from plant pathogenic bacteria, such as *Erwinia amylovora*. Inhibition of other pathogenic diseases may also be expected.

In accordance with the subject invention, novel methods, formulations and microorganisms are provided for inhibiting frost damage to host plants. The method is economical, efficient and can be readily applied at various stages of plant growth, such as to seeds, seed pieces, seedlings, buds and blooms. The presence of the ice nucleating deficient bacteria can be salutory, not only in inhibiting the presence of ice nucleating microorganisms, but disease causing microorganisms as well.

Although the foregoing invention has been described in some detail by way of illustration and example for purposes of clarity of understanding, it will be obvious that certain changes and modifications may be practiced within the scope of the appended claims.

I claim:

1. A method for inhibiting frost injury to a plant host susceptible to frost injury due to ice nucleation capable bacteria which comprises:
   applying to said host plant or a part thereof antagonistic nucleation deficient bacteria capable of substantially diminishing the availability of a limited nutrient provided by said host plant, whereby said antagonistic bacteria colonize said plant and inhibit colonization by ice nucleation capable bacteria.

2. A method according to claim 1, wherein said bacteria are obtained by mutagenesis of bacteria native to said host plant.

3. A method according to claim 1, wherein said plant part is seed or seed piece.

4. A method according to claim 3, wherein said ice nucleation deficient bacteria are applied as an aqueous suspension.

5. A method according to claim 3, wherein said ice nucleation deficient bacteria are applied as a powder.

6. A method according to claim 1, wherein said plant part is a bud.

7. A method according to claim 1, wherein said plant is a seedling.

8. A method according to any of claims 6 or 7, wherein said ice nucleation deficient bacteria are applied as a spray.

9. A method according to any of claims 6 or 7, wherein said ice nucleation deficient bacteria are applied as a powder.

10. A method for inhibiting frost injury to a plant host susceptible to frost injury due to ice nucleation capable bacteria, which method comprises:
    inoculating ice nucleation deficient bacteria on a nutrient medium which includes at least one nutrient, said nutrient being available in liminted amounts on said plant host;
    after a sufficient time for said ice nucleation deficient bacteria to form colonies, applying ice nucleation capable bacteria to the medium;
    isolating ice nucleation deficient bacteria from those colonies which are free from adjacent growth of the ice nucleation capable bacteria;
    growing said isolated bacteria; and
    applying said isolated bacteria or progeny thereof to said host plant or a part thereof.

11. A method according to claim 10, wherein said plant part is a seed or seed piece.

12. A method according to claim 11, wherein said selected bacteria are applied as an aqueous suspension.

13. A method according to claim 11, wherein said selected bacteria are applied as a powder.

14. A method according to claim 10, wherein said plant part is a bud.

15. A method according to claim 10, wherein said plant is a seedling.

16. A method according to any of claims 14 or 15, wherein said selected bacteria are applied as a spray.

17. A method according to any of claims 14 or 15, wherein said selected bacteria are applied as a powder.

* * * * *